(12) United States Patent
Klysz

(10) Patent No.: US 6,955,816 B2
(45) Date of Patent: Oct. 18, 2005

(54) ANTI-AGING SKIN CARE COMPOSITION AND USES THEREOF

(76) Inventor: Beatrice M. Klysz, 420 E. 55th St., New York, NY (US) 10022

( * ) Notice: Subject to any disclaimer, the term of this patent is extended or adjusted under 35 U.S.C. 154(b) by 0 days.

(21) Appl. No.: 10/294,375

(22) Filed: Nov. 14, 2002

(65) Prior Publication Data

US 2003/0095933 A1 May 22, 2003

Related U.S. Application Data

(60) Provisional application No. 60/331,455, filed on Nov. 16, 2001.

(51) Int. Cl.⁷ ................................................ A61K 7/00
(52) U.S. Cl. .......................... 424/401; 424/59; 424/69; 424/78.02; 514/276; 514/474
(58) Field of Search ........................... 424/401, 59, 69, 424/78.02; 514/276, 474

(56) References Cited

U.S. PATENT DOCUMENTS

| | | | |
|---|---|---|---|
| 4,704,280 A | 11/1987 | Bates | 424/195.1 |
| 5,292,538 A | * 3/1994 | Paul et al. | 426/74 |
| 5,541,220 A | 7/1996 | Ismail | 514/458 |
| 5,652,261 A | 7/1997 | Ismail | 514/458 |
| 5,786,384 A | 7/1998 | Ismail | 514/458 |
| 5,972,999 A | 10/1999 | Murad | 514/474 |
| 6,365,630 B1 | 4/2002 | Fisher et al. | 514/559 |
| 2002/0028844 A1 | 3/2002 | Fitzpatrick et al. | 514/474 |
| 2002/0064538 A1 | 5/2002 | Chung et al. | 424/401 |
| 2002/0106339 A1 | 8/2002 | Fisher et al. | 424/59 |
| 2002/0115723 A1 | 8/2002 | Iwasaki et al. | 514/616 |

FOREIGN PATENT DOCUMENTS

WO 9319743 10/1993

OTHER PUBLICATIONS

Vahlquist A, Rollman O, Holland DB, Cunliffe WJ. Isoretinoin treatment of severe acne affects the endogenous concentration of vitamin A in sebaceous glands. J Invest Dermatol 1990;94:496–498.

Ellis CN, Voorhees JJ. Treatment of actinically aged skin with topical tretioinPharmacol Skin 1989;3:249–252.

Lowe NJ, David M. Systemic retinoids in psoriasis: comparative efficacy and toxicity. Pharmacol Skin 1989;3:240–248.

* cited by examiner

Primary Examiner—Gary Kunz
Assistant Examiner—Konata M. George
(74) Attorney, Agent, or Firm—The Behr Office; Omri M. Behr

(57) ABSTRACT

The present invention is directed toward anti-aging skin care compositions comprising Vitamin B1, Vitamin B5, Vitamin C, N-acetyl-cysteine and, optionally, lipoic acid. The present invention is further directed toward methods for therapeutically or prophylactically treating the consequences of aging on the condition or appearance of the skin. The present invention further provides one or more kits that are useful for delaying, treating or preventing the consequences of aging on the condition or appearance of the skin.

15 Claims, No Drawings

ANTI-AGING SKIN CARE COMPOSITION AND USES THEREOF

CROSS REFERENCE TO RELATED APPLICATIONS

This application is a non-provisional application of U.S. Provisional Patent Application Ser. No. 60/331,455 of Klysz, filed Nov. 16, 2001, the contents of which are incorporated herein by reference.

INTRODUCTION

This invention relates to anti-aging skin care compositions for application to skin and to their use in improving the condition and appearance of skin. The present invention further relates to kits for use in improving the condition or appearance of skin, wherein the individual components of the anti-aging skin care composition may be packaged separately from, but may be readily combined with, its dermatologically-acceptable vehicle immediately prior to use. Such kits may facilitate ease of use, long-term storage, and/or efficacy of the anti-aging skin care composition.

BACKGROUND OF THE INVENTION

The appearance and condition of the skin may be degraded through the effects of environmental factors, either naturally occurring (sunlight, wind abrasion, humidity, etc.) or man-made (heating, air condition, pollutants, etc.), pathological processes such as dermatological diseases, or the normal aging process. The various insults to which the skin is exposed may act individually or synergistically.

To ameliorate or prevent the deterioration of skin quality that may occur over time, consumers have increasingly sought new and/or improved cosmetic compositions and cosmetic methods for skin care. Such products or methods are designed to prevent, delay or reverse the visible signs of the aging process, such as the appearance of wrinkles, lines, loss of skin tone, thinning of the skin, hyperpigmentation or mottling, and age spots. Such products or methods are further designed to improve the appearance and condition of sensitive, dry or flaky skin, and/or to soothe skin that has been irritated by exposure to chemicals, wind, or sunlight, among other potential irritants.

To meet consumer demand, many cosmetic compositions and cosmetic methods have been developed for skin care and treatment. However, many, if not most, of the products or treatment methods described to date lead to inadequate results or are marred by undesirable side effects. These may include irritation of the skin or adjacent mucous membranes, the production of excessive oiliness or greasiness of the skin, or discoloration of the skin.

Skin care products that have received considerable attention recently are those containing retinol (Vitamin A) or related compounds. Retinol, which is introduced into the body through the diet is metabolized to yield various derivatives called retinoids. Retinoids exert a variety of biological functions, including regulation of cellular proliferation, cellular differentiation and cell death. Retinoids are especially critical in the control of epithelial cell differentiation.

Natural and synthetic vitamin A derivatives (retinoids) have been used extensively in the treatment of a variety of skin disorders and have been used as skin repair or renewal agents. Retinoic acid, for example, has been employed to treat a variety of skin conditions, e.g. acne, wrinkles, psoriasis, age spots and discoloration. See e.g. Vahlquist et al., J. Invest. Dermatol. 1990; 94:496–498; Ellis et al., "Pharmacology of Retinols in Skin", Basel, Karger, Vol. 3, (1989), pp. 249–252; Lowe et al., "Pharmacology of Retinols in Skin", Vol. 3, (1989), pp. 240–248, PCT Patent Application No. WO 93/19743.

However, the use of products containing retinol or retinol derivatives can lead to mild side effects including but not limited to redness or stinging, itching, burning, skin scaling, peeling and dryness of the skin, or more severe side effects including but not limited to severe burning, itching, crusting, or swelling of the skin or alterations in skin pigmentation. Increased sensitivity to the environmental factors such as sunlight, wind or extremes in temperature also commonly occurs.

In light of these limitations, there continues to be a long-felt need for the development of improved cosmetic compositions and cosmetic methods for skin care and treatment that are both effective and fail to induce undesirable side effects. Toward this end, and as alternatives to products containing retinol or retinol derivatives, many researchers have examined topical anti-aging skin care compositions comprising various combinations of vitamins. For example, U.S. Published patent application Ser. No. 2002/0028844 discloses a combination of Vitamin C and Vitamin B5; U.S. Pat. No. 4,704,280 discloses a combination of Vitamin C and Vitamin B6; U.S. Pat. No. 5,541,220 discloses a combination of Vitamins C, B1, B2 and B6; related U.S. Pat. Nos. 5,652,261 and 5,786,384 disclose a combination of Vitamin C, Vitamin E, and a non-specified vitamin of the B series. Further, various combinations of Vitamin C and N-acetyl-cysteine are disclosed in U.S. Published patent application Ser. Nos. 2002/0115723, 2002/0106339, 2002/0064538, and in U.S. Pat. Nos. 5,972,999 and 6,365,630.

In contrast to the topical anti-aging skin care compositions listed above, the present invention comprises Vitamin B1, Vitamin B5, Vitamin C, N-acetyl-cysteine and, optionally, lipoic acid. When applied topically to the skin, the present invention can prevent or reverse cosmetically undesirable skin conditions such as wrinkles, lines, sagging, hyperpigmentation and age spots.

SUMMARY OF THE INVENTION

The present invention provides an anti-aging skin care composition comprising safe and effective amounts of: (a) Vitamin B1, (b) Vitamin B5, (c) Vitamin C, (d) N-acetyl-cysteine, and (e) a dermatologically acceptable vehicle. Optionally, the anti-aging skin care composition may further comprise lipoic acid.

The present invention further provides a method of providing at least one skin care benefit selected from the group consisting of: treating, delaying or preventing wrinkling; treating, delaying or preventing sagging; treating, delaying or preventing dry skin; treating, delaying or preventing photodamaged skin; treating, delaying or preventing formation of pimples or blackheads; closing pores; imparting a youthful appearance to skin; imparting fullness to lips; enhancing collagen deposition in skin; enhancing decorin production in skin; enhancing tissue repair; soothing irritated, red or sensitive skin; improving skin texture, smoothness or firmness; normalizing skin color by lightening or darkening skin; and limiting oil/sebum secretion; comprising applying to the skin the anti-aging skin care composition described above.

The present invention also provides for one or more kits for use in improving the condition or appearance of skin, wherein one or more of the individual components of the anti-aging skin care composition described above may be packaged separately, but may be readily combined to form the active anti-aging skin care composition described above immediately prior to use. Such kits may facilitate ease of use, long-term storage, and/or efficacy of the anti-aging skin care composition.

The inventive compositions, methods and uses described herein result in the prevention, reduction or delay in the formation of wrinkles, the prevention, reduction or delay in loss of skin tone, and the prevention, reduction or delay in the formation of pimples and blackheads. The compositions, methods and uses described herein also moderate skin discolorations such as brown spots, age spots or liver spots, rejuvenate dry, abused, or irritated skin, close or tighten pores, improve skin texture, smoothness or firmness, and create smooth and supple skin with improved elasticity. A general improvement in the appearance, texture and condition, in particular with respect to the radiance, clarity, and general youthful appearance of skin is achieved. The present invention therefore provides a wide range of results that are collectively described as anti-aging benefits.

BRIEF DESCRIPTION OF THE DRAWINGS

Not applicable

Definitions

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, etc.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e. to provide a reasonable benefit to risk ratio, within the scope of sound judgment of the skilled artisan.

The term "skin compatibility," as used herein means the ability of skin to tolerate long term application of topical compositions with minimal adverse skin reactions such as stinging, burning, redness, itching and folliculitis.

DETAILED DESCRIPTION OF THE INVENTION

The present invention provides an anti-aging skin care composition comprising: (a) Vitamin B1, (b) Vitamin B5, (c) Vitamin C, (d) N-acetyl-cysteine, and (e) a dermatologically acceptable vehicle. The anti-aging skin care composition may further comprise lipoic acid.

In preferred embodiments, the anti-aging skin care composition contains between from about 100 mg to 1000 mg of Vitamin B1, from about 200 mg to 1000 mg of Vitamin B5, from about 2000 mg to 5000 mg of Vitamin C, from about 400 mg to 1200 mg of N-acetyl-cysteine, from about 0 mg to 500 mg of lipoic acid; hereinafter referred to as "active ingredients," a dermatologically-acceptable vehicle, wherein the ratio between the mixture of the active ingredients and the dermatologically-acceptable vehicle is approximately 1:12, as calculated on a weight to weight basis (w/w). However, in various other preferred embodiments, this ratio may range from about 1:12 to 1:1 (w/w). This variation of ranges permits the potency of the anti-aging skin care composition to be tailored to the needs of the individual subject, based on the location of the skin to be treated (i.e. face, hands, arms, etc.), skin care type, and the nature of the exposure to various skin irritants such as sunlight, wind abrasion, etc.

As indicated above, the anti-aging skin care composition of the present invention also comprises a dermatologically-acceptable vehicle. This substance may act as a dilutant, dispersant or carrier for the active ingredients. The vehicle may comprise materials commonly employed in skin care products, including but not limited to water, a buffered aqueous solution, liquid or solid emollients, silicone oils, emulsifiers, solvents, humectants, thickeners, powders, propellants and the like. The vehicle may constitute from approximately 5% to 99.9% by volume of the anti-aging skin care composition, but preferably will constitute from approximately 50% to 95% by volume of the anti-aging skin care composition. In the absence of the other potential cosmetic or manufacturing adjuncts described below, the dermatologically-acceptable vehicle will constitute the balance of the composition.

The powdered components of the anti-aging skin care composition may be dissolved in more or less vehicle to increase or decrease the strength and hence the potency of the product. Such variations in strength and potency may be highly desirable in maintaining the efficacy of the anti-aging skin care composition when treating a highly heterogeneous population comprised of individuals with large variations in skin type and condition. In preferred embodiments, the ratio of active ingredients to vehicle ranges from 1:12 (weight to weight; w/w) to 1:1 (w/w).

In addition to the active ingredients described above, the anti-aging skin care composition of the present invention may optionally contain various cosmetic or manufacturing adjuncts. For example, sunscreens, skin-lightening or skin-tanning agents may also be included. The vehicle may also further include adjuncts such as antioxidants, perfumes, opacifiers, preservatives, colorants and buffers, as necessary or desirable to enhance the efficacy, storage, utility, or marketability of the anti-aging skin care composition. Vitamin E and its derivatives are especially preferred among potential antioxidant compounds. In preferred embodiments, the addition of perfumes or other masking agents to the skin care composition is desirable and/or necessary to reduce or block the odors associated with the presence of the active ingredients. For orally-ingested forms of the invention, excipients or other materials may be added.

To prepare the anti-aging skin care composition of the present invention, a variety of techniques may be employed. For example, the active ingredients may be generally incorporated into the dermatologically-acceptable vehicle in the manner that is usual for the preparation of skin care products. Thus, the active ingredients may first be dissolved or dispersed in a portion of the water or another solvent or liquid to be incorporated into the dermatologically-acceptable vehicle. The preferred compositions for use in this manufacturing approach are oil-in-water, water-in-oil, or water-in-oil-in-water emulsions.

However, in a preferred embodiment, the active ingredients, with or without the above-described adjuncts, are maintained in a separate state from the dermatologically-acceptable carrier, for example as a dry powder. The inter-mixing of the desired amount of pre-mixed active ingredients with the desired amount of vehicle, performed by the consumer immediately prior to application of the anti-aging skin care composition, ensures that the product will retain its maximum efficacy, and will also permit the potency of the product to be tailored to the individual needs of the user. The resulting anti-aging skin care composition then may be applied to the skin of the face, hands, arms, legs, neck or other areas where treatment is desirable by manual application, by spraying, or by any other method suitable to ensure complete and even coverage of the treated areas.

The anti-aging skin care composition of the present invention may be in the form of conventional "leave-on" skin-care products, including but not limited to aqueous solutions, creams, gels, lotions, sprays, ointments, pastes, mousses, cosmetics, etc. The anti-aging skin care composition can also be in the form of "wash-off" products, including but not limited to, a bath or shower gel, possibly containing a delivery system for the active ingredients to promote their adsorption or adherence to the skin during rinsing. Most preferably the product is a "leave-on" product; a product to be applied to the skin without a deliberate rinsing step soon after its application to the skin.

The anti-aging skin care composition of the present invention may be packaged in any suitable manner, including but not limited to, a jar, a bottle, a tube, a stick, a roller-ball applicator, an aerosol spray device, etc., in the conventional manner. As indicated above, it is also contemplated that the anti-aging skin care composition could be packaged as a kit of two or more separate compartments, including one containing the active ingredients and a second containing the dermatologically-acceptable vehicle, which may be mixed together at some fixed time point prior to application. For example, the active ingredients, in the form of a powder, a tablet, a capsule or a liquid, may be contained in sealed, single-use packets, which may be opened and mixed with the dermatologically-acceptable vehicle, which may also be stored in pre-measured form in sealed, single-use packets. Alternatively, the active ingredients and the dermatologically-acceptable vehicle may be provided in larger quantities from which the needed amount could be withdrawn using various measuring devices, such as a measuring spoon or cup for solids, or a calibrated vial or dropper for liquids.

Anti-aging skin care compositions of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Each unit dose may be divided between one or more tablets, cachets or capsules. In a preferred embodiment, a safe and effective daily dose of the active ingredients is contained within two or less tablets, cachets or capsules.

The present invention further provides a method of providing at least one skin care benefit selected from the group consisting of: treating, delaying or preventing wrinkling; treating, delaying or preventing sagging; treating, delaying or preventing dry skin; treating, delaying or preventing photodamaged skin; treating, delaying or preventing formation of pimples or blackheads; closing pores; imparting a youthful appearance to skin; imparting fullness to lips; enhancing collagen deposition in skin; enhancing decorin production in skin; enhancing tissue repair; soothing irritated, red or sensitive skin; improving skin texture, smoothness or firmness; normalizing skin color by lightening or darkening skin; and limiting oil/sebum secretion; comprising applying to the skin the anti-aging skin care composition described above.

In preferred embodiments, the method of the present invention may be carried out one or more times daily to the skin which requires treatment. In this method, a small volume of the anti-aging skin care composition, for example from 0.1 to 5 ml, is applied to the skin from a suitable container or applicator and spread over and/or rubbed into the skin using the hands or fingers or a suitable device. A rinsing step may optionally follow depending on whether the composition is formulated as a "leave-on" or a "rinse-off" product. The improvement in skin appearance will become apparent within one or more days of use, depending on skin condition and the concentration, amount and frequency with which the anti-aging skin care composition is used.

In other embodiments, wherein more dramatic or more immediate results are desired, the method of the present invention may be carried out through the intra- or sub-dermal injection of the anti-aging skin care composition. In these embodiments, the anti-aging skin care composition, in a suitably sterile form, would be administered by a licensed practitioner, such as a dermatologist, directly to the area to be treated.

The inventive compositions, methods and uses described herein result in the prevention, reduction or delay in the formation of wrinkles, the prevention, reduction or delay in loss of skin tone, and the prevention, reduction or delay in the formation of pimples and blackheads. The compositions, methods and uses described herein also moderate skin discolorations such as brown spots, age spots or liver spots, rejuvenate dry, abused, or irritated skin, close or tighten pores, improve skin texture, smoothness or firmness, and create smooth and supple skin with improved elasticity, A general improvement in the appearance, texture and condition, in particular with respect to the radiance, clarity, and general youthful appearance of skin is achieved. The present invention therefore provides a wide range of results that are collectively described as anti-aging benefits.

The inventive compositions, methods and uses described herein are further useful for topical application and for regulating skin condition, including visible and/or tactile discontinuities in skin (especially the skin surface; such discontinuities are generally undesirable). Such discontinuities may be induced or caused by internal and/or external factors, and include the signs of skin aging described herein. The term "treating skin condition" includes prophylactically and/or therapeutically treating skin condition, including visible and/or tactile discontinuities in skin. As used herein, prophylactically treating skin condition includes delaying, minimizing and/or preventing visible and/or tactile discontinuities in skin. As used herein, therapeutically treating skin condition includes ameliorating, e.g. diminishing, minimizing and/or effacing, discontinuities in skin. Treating skin condition improves skin appearance and/or feel.

The inventive compositions, methods and uses described herein are further useful for treating signs of skin aging, more especially visible and/or tactile discontinuities in skin texture associated with aging. "Treating the signs of skin aging" includes prophylactically and/or therapeutically treating one or more of such signs (similarly, regulating a given sign of skin aging, e.g. lines, wrinkles or pores, includes prophylactically treating and/or therapeutically treating that sign). As used herein, prophylactically treating such signs includes delaying, minimizing and/or preventing signs of skin aging. As used herein, therapeutically treating such signs includes ameliorating, e.g. diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g. chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g. associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, redness or discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g. telangiectasia or spider vessels), and underlying tissues, especially those proximate to the skin.

It is to be understood that the present invention is not to be limited to treatment of the above mentioned "signs of skin aging" which arise due to mechanisms associated with skin aging, but is intended to include treatment of said signs irrespective of the mechanism of origin. As used herein, "treating skin condition" is intended to include treatment of such signs irrespective of the mechanism of origin.

The present invention is especially useful for therapeutically treating visible and/or tactile discontinuities in mammalian skin texture, including texture discontinuities associated with skin aging. As used herein, therapeutically treating such discontinuities includes ameliorating, e.g. diminishing, minimizing and/or effacing visible and/or tactile discontinuities in the texture of mammalian skin, to thereby provide improved skin appearance and/or feel, e.g. a smoother, more even appearance and/or feel. Such visible and/or tactile discontinuities in skin texture include crevices, bumps, pores, fine lines, wrinkles, scales, flakes and/or other forms of textural unevenness or roughness associated with skin aging or irritation. For example, the length, depth, and/or other dimension of lines and/or wrinkles are decreased, the apparent diameter of pores decreases, or the apparent height of tissue immediately proximate to pore openings approaches that of the interadnexal skin.

The present invention is also especially useful for prophylactically treating visible and/or tactile discontinuities in mammalian skin texture, including texture discontinuities associated with skin aging or irritation. As used herein, prophylactically treating such discontinuities includes delaying, minimizing and/or preventing visible and/or tactile discontinuities in the texture of mammalian skin or in its appearance, to thereby provide improved skin appearance and/or feel, e.g. a smoother, more even appearance and/or feel.

EXAMPLES

So that it may be more readily understood, the present invention is illustrated in, but not limited to, the following examples.

Comparative Example 1

Topical Application of an Aqueous Solution of Vitamin C. A one gram tablet of Vitamin C (Ascorbic acid; GNC Brand, GNC, Inc.) was dissolved to completion in 1 tablespoon of water. The resulting solution was applied to the facial skin of a human subject immediately before bedtime. Upon initial contact with the facial skin, a slight burning sensation was evident, but the sensation abated once the solution dried.

Upon waking after approximately 6–8 hrs of sleep, a slight redness of the facial skin was noticed as compared to other skin surfaces not treated by the Vitamin C solution. However, the appearance of the facial skin was noticeably improved, with an enhancement of the radiance and clarity of the skin, increased skin tone, smaller and less evident pores, and better skin texture, smoothness and firmness. Moreover, the minor redness and irritation evident upon the initial application subsided greatly following subsequent applications, even as the dose of Vitamin C was increased to 2 g. and ultimately to as much as 5 g. (see below).

Comparative Example 2

Direct Comparisons of Aqueous Vitamin C Solution to Aqueous Vitamin C Solutions Containing Additional Ingredients. Several direct comparisons were performed to determine whether the addition of additional components could improve the results observed with Vitamin C alone. In the first of these tests, an aqueous solution comprising Vitamin C alone (3 g) was applied to one side of the subject's face immediately before bedtime, while an aqueous solution comprising 3 g of Vitamin C and 600 mg of N-acetyl-cysteine (GNC, Inc.) was applied to the other half of the subject's face at the same time. The solution containing Vitamin C and N-acetyl-cysteine could be applied more smoothly than the solution containing Vitamin C alone. Furthermore, the stinging or burning sensation was less evident following application of the solution containing N-acetyl-cysteine.

Upon waking after approximately 6–8 hrs of sleep, the appearance of the skin receiving the combination of Vitamin C and N-acetyl-cysteine was noticeably superior to that of the skin receiving Vitamin C only. The combination of Vitamin C and N-acetyl-cysteine was better able to remove or lessen fine lines and produced tighter, firmer, fresher looking skin than Vitamin C alone.

A second comparison was then performed. In this study, an aqueous solution comprising Vitamin C (3 g) and Vitamin B5 (500 mg, obtained from GNC, Inc.) was applied to one side of the subject's face immediately before bedtime, while an aqueous solution comprising 3 g of Vitamin C, 600 mg of N-acetyl-cysteine and 10 mg zinc (GNC, Inc.) was applied to the other half of the subject's face at the same time. Neither solution could be applied as smoothly as the solution containing Vitamin C alone. However, after an overnight application, the combination of Vitamin C and zinc yielded results that were superior when compared to those achieved by the combination of Vitamin C and Vitamin B5, especially with regard to the smoothness of the skin. Unfortunately, the addition of zinc increased the odor of the composition.

Comparative Example 3

Addition of Vitamin E Prevented by Poor Solubility. Although Vitamin E is well-known as an anti-oxidant, and therefore its inclusion in an anti-aging skin care composition may be highly desirable, neither oils nor powders containing Vitamin E were miscible with the aqueous solution containing Vitamin C. Thus, no further studies of the effects of the addition of Vitamin E to the various anti-aging skin care compositions described herein were performed.

Example 4

Topical Application of an Aqueous Solution of Vitamin C, Vitamin B1, Vitamin B5 and N-acetyl-cysteine. Based on the success of the studies described in Example 2, several additional components were then added to the aqueous Vitamin C solution to further improve its effects on skin condition and appearance. The ingredients, which included Vitamin B1, Vitamin B5 and N-acetyl-cysteine, were chosen for their known or reported effects on the renewal of skin, nails or hair when ingested.

Tablets containing 3 g of Vitamin C, 100 mg of Vitamin B1, 500 mg of Vitamin B5 and 500 mg of N-acetyl-cysteine, all obtained from obtained from GNC, Inc., were ground into a powder and mixed together. The mixture was then added to one tablespoon of water and allowed to dissolve to completion, which took approximately 10 hrs. The resulting solution was applied to the facial skin of a human subject immediately before bedtime. Upon initial contact with the facial skin, a slight burning or stinging sensation was again evident, which was slightly stronger than that experienced in response to Vitamin C alone, as well as some mild itchiness. As was observed with the solution containing Vitamin C alone, these sensations largely subsided once the solution was dried.

Even prior to sleeping, a tightening or firming of the skin was noticeable following drying of the solution. Upon waking after approximately 6–8 hrs of sleep, a slight redness of the facial skin was again present, but the appearance of the facial skin was noticeably improved. In addition to the improvements seen above with Vitamin C alone, the presence of minor skin blemishes such as blackheads, pimples or brown liver- or age-spots was much less apparent. Individuals having no prior knowledge of the use of this anti-aging skin care composition remarked on the quality and appearance of the subject's facial skin.

Example 5

Variation of the Amounts of Vitamin C Fails to Significantly Improve Anti-aging Skin Care Composition. Optimization of ranges for each of the components was determined. For example, the amount of Vitamin C present in the composition described above in Example 2 was varied from 0 g to 5 g. Compositions containing doses of Vitamin C less than 2 g had no effect or only an undesirably weak effect on skin quality and appearance. Compositions containing doses of Vitamin C ranging from 2 g to 5 g yielded largely similar effects. Thus, 2 g to 5 g may represent an optimal range for Vitamin C in the anti-aging skin care compositions disclosed herein.

Example 6

Addition of Lipoic Acid Reduces Irritation While Maintaining Beneficial Effects of Anti-aging Skin Care Composition. In an attempt to reduce the slight irritation caused by application of the anti-aging skin care composition and to enhance its effects on fine lines and wrinkles, 100 mg of lipoic acid was added to the anti-aging skin care composition comprising 3 g of Vitamin C, 100 mg of Vitamin B1, 500 mg of Vitamin B5 and 500 mg of N-acetyl-cysteine. For these studies, all ingredients, obtained in powdered form from for example GNC, Inc. or Mother Nature, Inc. among other possible suppliers, were mixed together and ¼ teaspoon of the resulting mixture was dissolved to completion in 1 tablespoon of water, the complete dissolution occurring within a few seconds. The resulting solution was again applied to the facial skin of a human subject immediately before bedtime. As with the previous compositions described above, there was some mild stinging or burning of the skin immediately after application that subsided upon drying, when the skin also became noticeably tighter.

Upon waking after approximately 6–8 hrs of sleep, a slight burning persisted, but did not last throughout the day. The appearance of the facial skin was noticeably enhanced along the lines seen after application of the anti-aging skin care compositions described above, but with some additional improvements. Fine lines and wrinkles became progressively less noticeable. The skin became thicker, plumper, and not sensitized to heat, cold, sun or wind, as may occur after using other skin care products, especially those containing retinol or its derivatives. Qualitatively similar results were obtained when the amount of Vitamin C in this composition was increased to 4 g and then to 5 g.

Example 7

Storage of the Anti-aging Skin Care Composition. Because some of the components of the anti-aging skin care composition are highly hygroscopic and/or photodegradable, proper storage conditions are necessary to retain the efficacy of the anti-aging skin care composition. For example, when left in the open, the powder mixture rapidly absorbs water from the atmosphere and becomes unusable. Similarly, prolonged exposure to light leads to reduced efficacy. Storage of the product in sealed plastic bags solves at least in part the hygroscopicity problem, but does not deter photodegradation. Through direct experimentation, optimal storage conditions were determined to comprise tightly-sealed, dark-colored glass or plastic bottles.

All references cited herein are incorporated herein in their entirety.

I claim:

1. An anti-skin aging composition consisting essentially of
   a) from about 100 mg to 1000 mg of Vitamin B1;
   b) from about 200 mg to 1000 mg of Vitamin B5;
   c) from about 2000 mg to 5000 mg of Vitamin C;
   d) from about 400 mg to 1200 mg of N-acetyl-cysteine; and
   e) from about 0 mg to 500 mg of lipoic acid.

2. An anti-skin aging composition of claim 1 consisting essentially of:
   a) from about 100 mg to 1000 mg of Vitamin B1;
   b) from about 200 mg to 1000 mg of Vitamin B5;
   c) from about 2000 mg to 5000 mg of Vitamin C;

d) from about 400 mg to 1200 mg of N-acetyl-cysteine;

e) from about 0 mg to 500 mg of lipoic acid; and f) a dermatologically-acceptable vehicle, wherein the ratio between a mixture comprising said Vitamin B1, said Vitamin B5, said Vitamin C, said N-acetyl-cysteine, and said lipoic acid and said dermatologically-acceptable vehicle is from about 1:12 to 1:1.

3. A method for therapeutically or prophylactically treating signs of skin aging in a mammalian subject comprising administering to said subject a safe and effective amount of the composition of claim 2.

4. The composition of claim 2 further comprising one or more cosmetic or manufacturing adjuncts selected from the group consisting of a sunscreen, a skin-lightening agent, a skin-tanning agent, an antioxidant, a perfume, an opacifier, a preservative, a colorant an emulsifier, a thickener and a buffer.

5. The composition of claim 2, wherein said dermatologically-acceptable vehicle is selected from the group consisting of water, a buffered aqueous solution, a liquid emollient, or solid emollient, a silicone oil, and a solvent.

6. The composition of claim 2, wherein said ratio between said mixture of Vitamin B1, Vitamin B5, Vitamin C, N-acetyl-cysteine and lipoic acid and said dermatologically-acceptable vehicle is about 1:12.

7. The composition of claim 2, wherein said dermatologically-acceptable vehicle is water.

8. The composition of claim 2, wherein said composition is in the form of an aqueous solution, a lotion, a cream, a stick, a spray, an ointment, a paste, a mousse, or a cosmetic.

9. A method for therapeutically or prophylactically treating signs of skin aging in a mammalian subject comprising administering to said subject a safe and effective amount of the composition of claim 2.

10. The method of claim 9, wherein the route of delivery is topical, oral, or by intradermal or subdermal injection.

11. The method of claim 3, wherein the route of delivery is topical, oral, or by intradermal or subdermal injection.

12. The method of claim 3, wherein the route of delivery is topical.

13. The method of claim 3 which comprises the step of mixing the components (a) to (e) inclusive with component (f) just before administration thereof.

14. The method of claim 13 wherein the dermatologically acceptable vehicle is selected from the group consisting of water, a buffered aqueous solution, a liquid emollient, a solid emollient, and a solvent.

15. The method of claim 13, wherein said ratio between said mixture of Vitamin B1, Vitamin B5, Vitamin C, N-acetyl-cysteine and lipoic acid and said dermatologically-acceptable vehicle is about 1:12.

* * * * *